United States Patent
Lee et al.

(10) Patent No.: US 10,081,822 B2
(45) Date of Patent: Sep. 25, 2018

(54) **MICROORGANISM OF THE GENUS *ESCHERICHIA* PRODUCING L-TRYPTOPHAN AND METHOD FOR PRODUCING L-TRYPTOPHAN USING THE SAME**

(71) Applicant: CJ Cheiljedang Corporation, Seoul (KR)

(72) Inventors: Seok Myung Lee, Seoul (KR); Baek Seok Lee, Seoul (KR); Kyungrim Kim, Seoul (KR); Kwang Ho Lee, Daejeon (KR); Keun Cheol Lee, Gyeonggi-do (KR); Hyeongpyo Hong, Gangwon-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/573,236

(22) PCT Filed: May 10, 2016

(86) PCT No.: PCT/KR2016/004893
§ 371 (c)(1),
(2) Date: Nov. 10, 2017

(87) PCT Pub. No.: WO2016/182321
PCT Pub. Date: Nov. 17, 2016

(65) Prior Publication Data
US 2018/0087077 A1    Mar. 29, 2018

(30) Foreign Application Priority Data
May 14, 2015    (KR) ........................ 10-2015-0067660

(51) Int. Cl.
| | |
|---|---|
| *C12N 9/16* | (2006.01) |
| *C12P 13/22* | (2006.01) |
| *C12Q 1/68* | (2018.01) |
| *C12N 1/20* | (2006.01) |
| *C12N 15/00* | (2006.01) |
| *C07H 21/04* | (2006.01) |
| *C12N 15/70* | (2006.01) |
| *C12P 13/14* | (2006.01) |

(52) U.S. Cl.
CPC .............. *C12P 13/227* (2013.01); *C12N 1/20* (2013.01); *C12N 15/70* (2013.01); *C12P 13/14* (2013.01)

(58) Field of Classification Search
None
See application file for complete search history.

(56) References Cited

U.S. PATENT DOCUMENTS 8,435,765 B2    5/2013 Abraham et al.

FOREIGN PATENT DOCUMENTS

| KR | 1987-0001813 B1 | 10/1987 |
|---|---|---|
| KR | 10-1997-0001533 A | 1/1997 |
| KR | 10-2005-0059685 A | 6/2005 |
| KR | 10-0792095 B1 | 1/2008 |
| KR | 10-2009-0075549 A | 7/2009 |
| KR | 10-1261147 B1 | 5/2013 |
| KR | 10-2013-0082121 A | 7/2013 |

OTHER PUBLICATIONS

Datsenko et al. 2000. One-step inactivation of chromosomal genes in *Escherichia coli* K-12 using PCR products. *Proc. Natl. Acad. Sci. USA*, 97(12):6640-6645.
Faghfuri et al. 2013. L-tryptophan production by whole cells of *Escherichia coli* based on Iranian sugar beet molasses. *Jundishapur Journal of Microbiology*, 6(4):e5370.
Kuznetsova et al. 2006. Genome-wide analysis of substrate specificities of the *Escherichia coli* haloacid dehalogenase-like phosphatase family. *Journal of Biological Chemistry*, 281(47):36149-36161.
NCBI Genbank Accession No. CDP77019. May 11, 2014. Putative hydrolase [*Escherichia coli* D6-117.29], 2 pages.
NCBI Genbank Accession No. WP_000285362.1. Mar. 22, 2015. Multispecies: pyridoxal phosphate phosphatase YigL [Enterobacteriaceae], 1 page.
Palmeros et al. 2000. A family of removable cassettes designed to obtain antibiotic-resistance-free genomic modifications of *Escherichia coli* and other bacteria. *Gene*, 247:255-264.
Sun et al. 2013. Physiological consequences of multiple-target regulation by the small RNA SgrS in *Escherichia coli*. *Journal of Bacteriology*, 195(21):4804-4815.
Talukder et al. 2005. Analysis of reading frame and expressional regulation of randomly selected promoter-proximal genes in *Escherichia coli*. *J. Gen. Appl. Microbiol.*, 51:93-103.
International Search Report dated Sep. 7, 2016 for International Application No. PCT/KR2016/004893 filed May 10, 2016, 10 pages.
Written Opinion dated Sep. 7, 2016 for International Application No. PCT/KR2016/004893 filed May 10, 2016, 4 pages.
Gu, et al. "One-step of tryptophan attenuator inactivation and promoter swapping to improve the production of L-tryptophan in *Escherichia coli*", Microbial Cell Factories, 11:30, pp. 1-9, 2012.
NCBI GenBank, AAT48225.1 (www.ncbi.nlm.nih.gov/protein/AAT48225.1).
Office Action in Chinese Patent Application No. 201680000670.0, dated Jul. 24, 2018.
Papenfort et al., "Small RNA-Mediated Activation of Sugar Phosphatase mRNA Regulates Glucose Homeostasis", Elsevier, Cell 153:426-437, Apr. 11, 2013.

*Primary Examiner* — Yong D Pak
(74) *Attorney, Agent, or Firm* — Knobbe Martens Olson & Bear LLP

(57) ABSTRACT

The present invention relates to a microorganism of the genus *Escherichia* in which L-tryptophan productivity is improved by inactivating phosphatase activity. Further, the present invention relates to a method for producing L-tryptophan using the microorganism of the genus *Escherichia*.

4 Claims, No Drawings
Specification includes a Sequence Listing.

SEQUENCE LISTING

<160> NUMBER OF SEQ ID NOS: 8

<210> SEQ ID NO 1
<211> LENGTH: 266
<212> TYPE: PRT
<213> ORGANISM: Escherichia

<400> SEQUENCE: 1

```
Met Tyr Gln Val Val Ala Ser Asp Leu Asp Gly Thr Leu Leu Ser Pro
 1               5                  10                  15

Asp His Thr Leu Ser Pro Tyr Ala Lys Glu Thr Leu Lys Leu Leu Thr
             20                  25                  30

Ala Arg Gly Ile Asn Phe Val Phe Ala Thr Gly Arg His His Val Asp
         35                  40                  45

Val Gly Gln Ile Arg Asp Asn Leu Glu Ile Lys Ser Tyr Met Ile Thr
     50                  55                  60

Ser Asn Gly Ala Arg Val His Asp Leu Asp Gly Asn Leu Ile Phe Ala
 65                  70                  75                  80

His Asn Leu Asp Arg Asp Ile Ala Ser Asp Leu Phe Gly Val Val Asn
                 85                  90                  95

Asp Asn Pro Asp Ile Ile Thr Asn Val Tyr Arg Asp Asp Glu Trp Phe
            100                 105                 110

Met Asn Arg His Arg Pro Glu Glu Met Arg Phe Phe Lys Glu Ala Val
        115                 120                 125

Phe Gln Tyr Ala Leu Tyr Glu Pro Gly Leu Leu Glu Pro Glu Gly Val
    130                 135                 140

Ser Lys Val Phe Phe Thr Cys Asp Ser His Glu Gln Leu Leu Pro Leu
145                 150                 155                 160

Glu Gln Ala Ile Asn Ala Arg Trp Gly Asp Arg Val Asn Val Ser Phe
                165                 170                 175

Ser Thr Leu Thr Cys Leu Glu Val Met Ala Gly Gly Val Ser Lys Gly
            180                 185                 190

His Ala Leu Glu Ala Val Ala Lys Lys Leu Gly Tyr Ser Leu Lys Asp
        195                 200                 205

Cys Ile Ala Phe Gly Asp Gly Met Asn Asp Ala Glu Met Leu Ser Met
    210                 215                 220

Ala Gly Lys Gly Cys Ile Met Gly Ser Ala His Gln Arg Leu Lys Asp
```

```
                225                 230                 235                 240
            Leu His Pro Glu Leu Glu Val Ile Gly Thr Asn Ala Asp Asp Ala Val
                            245                 250                 255

Pro His Tyr Leu Arg Lys Leu Tyr Leu Ser
                        260                 265

<210> SEQ ID NO 2
<211> LENGTH: 801
<212> TYPE: DNA
<213> ORGANISM: Escherichia
<220> FEATURE:
<221> NAME/KEY: gene
<222> LOCATION: (1)..(801)
<223> OTHER INFORMATION: yigL

<400> SEQUENCE: 2
atgtaccagg ttgttgcgtc tgatttagat ggcacgttac tttctcccga ccatacgtta      60
tccccttacg ccaaagaaac tctgaagctg ctcaccgcgc gcggcatcaa ctttgtgttt     120
gcgaccggtc gtcaccacgt tgatgtgggg caaattcgcg ataatctgga gattaagtct     180
tacatgatta cctccaatgg tgcgcgcgtt cacgatctgg atggtaatct gattttgct      240 cataacctgg atcgcgacat tgccagcgat ctgtttggcg tagtcaacga caatccggac     300
atcattacta acgtttatcg cgacgacgaa tggtttatga atcgccatcg cccggaagag     360
atgcgctttt ttaaagaagc ggtgttccaa tatgcgctgt atgagcctgg attactggag     420
ccggaaggcg tcagcaaagt gttcttcacc tgcgattccc atgaacaact gctgccgctg     480
gagcaggcga ttaacgctcg ttggggcgat cgcgtcaacg tcagtttctc taccttaacc     540
tgtctggaag tgatggcggg cggcgtttca aaaggccatg cgctggaagc ggtggcgaag     600
aaactgggct acagcctgaa ggattgtatt gcgtttggtg acgggatgaa cgacgccgaa     660
atgctgtcga tggcggggaa aggctgcatt atgggcagtg cgcaccagcg tctgaaagac     720
cttcatcccg agctggaagt gattggtact aatgccgacg acgcggtgcc gcattatctg     780
cgtaaactct atttatcgta a                                               801

<210> SEQ ID NO 3
<211> LENGTH: 70
<212> TYPE: DNA
<213> ORGANISM: Artificial Sequence
<220> FEATURE:
<223> OTHER INFORMATION: YIGL-CM-R2 Primer

<400> SEQUENCE: 3
ttgcgtctga tttagatggc acgttacttt ctcccgacca tacgttatcc tagtggatct      60
gatgggtacc                                                             70

<210> SEQ ID NO 4
<211> LENGTH: 70
<212> TYPE: DNA
<213> ORGANISM: Artificial Sequence
<220> FEATURE:
<223> OTHER INFORMATION: yigL-R1 Primer

<400> SEQUENCE: 4
cccagcggaa accgctctac agaggtttaa atttcttatg taccaggttg ttgcgtctga      60
tttagatggc                                                             70

<210> SEQ ID NO 5
<211> LENGTH: 70
```

```
<212> TYPE: DNA
<213> ORGANISM: Artificial Sequence
<220> FEATURE:
<223> OTHER INFORMATION: yigL-Cm-F2 Primer

<400> SEQUENCE: 5
ccattgtagc gaagtatcag gttgacaact gaccaaataa agaacgatta aggtgacact    60
atagaacgcg                                                          70

<210> SEQ ID NO 6
<211> LENGTH: 70
<212> TYPE: DNA
<213> ORGANISM: Artificial Sequence
<220> FEATURE:
<223> OTHER INFORMATION: yigL-F1 Primer

<400> SEQUENCE: 6
tggtgatgat aagtagcgcc acaatggaaa actctttgat taacgggtat ccattgtagc    60
gaagtatcag                                                          70

<210> SEQ ID NO 7
<211> LENGTH: 20
<212> TYPE: DNA
<213> ORGANISM: Artificial Sequence
<220> FEATURE:
<223> OTHER INFORMATION: yigL conF1 Primer

<400> SEQUENCE: 7
aaccgcatgc atgaccgttt                                               20

<210> SEQ ID NO 8
<211> LENGTH: 20
<212> TYPE: DNA
<213> ORGANISM: Artificial Sequence
<220> FEATURE:
<223> OTHER INFORMATION: yigL conR1 Primer

<400> SEQUENCE: 8
atatacaggc cgaccgtttt                                               20
```

MICROORGANISM OF THE GENUS *ESCHERICHIA* PRODUCING L-TRYPTOPHAN AND METHOD FOR PRODUCING L-TRYPTOPHAN USING THE SAME

CROSS-REFERENCE TO RELATED APPLICATIONS

This application is a U.S. National Phase Application of PCT International Application No. PCT/KR2016/004893, filed on May 10, 2016, designating the United States of America, which is an International Application of and claims the benefit of priority to Korean Patent Application No. 10-2015-0067660, filed on May 14, 2015.

SEQUENCE LISTING STATEMENT

The present application contains a Sequence Listing, which is being submitted vis EFS-Web on even date herewith. The Sequence Listing is submitted in a filed entitled "Sequence_Listing_HAN030-002APC.txt," which was created on Nov. 7, 2017, and is approximately 5 kb in size. This Sequence Listing is hereby incorporated by reference.

TECHNICAL FIELD

The present invention relates to a modified microorganism of the genus *Escherichia* producing L-tryptophan, wherein the activity of phosphatase is inactivated, and a method for producing L-tryptophan using the microorganism of the genus *Escherichia*.

BACKGROUND ART

L-tryptophan, which is an essential amino acid, has been widely used as a feed additive, a base material for medicines such as transfusion agents, etc., and a base material for health functional foods, etc. Although such L-tryptophan may be produced by chemosynthesis, enzyme reaction, fermentation methods, etc., L-tryptophan is mainly produced by direct fermentation using microorganisms at present. In early stages, the development of L-tryptophan-producing strains was carried out by mutation selection (Korean Patent Application Publication No. 1987-0001813). Along with the development of genetic engineering, the development of tryptophan-producing strains was carried out by a method for overcoming tryptophan feedback inhibition of enzymes in biosynthetic pathways via the enhancement of enzyme synthesis in metabolic processes, as in enhancing the expression of tryptophan biosynthetic enzymes. However, it is still required to develop tryptophan-producing strains having highly efficient production for industrial use.

In particular, tryptophan synthase (EC 4.2.1.20), which takes part in the final reaction stage during tryptophan biosynthesis by microorganisms, is known to use pyridoxal phosphate (PLP) as a coenzyme. Further, in the case of serine, which is used as a substrate for the tryptophan synthase reaction, phosphohydroxythreonine aminotransferase (EC 2.6.1.52) encoded by serC uses PLP as a coenzyme, and thus, PLP is considered to be an important coenzyme for tryptophan biosynthesis.

Therefore, maintaining an appropriate PLP concentration is expected to play an important role in effective reactions for the corresponding enzymes and biosynthetic reactions for the desired products. However, the coenzymes contribute to various reactions besides the tryptophan production, and therefore, a method for properly maintaining PLP level has not been discovered yet. In addition, it still remains to be elucidated whether the maintenance of PLP level in tryptophan-producing microorganisms could lead to an increase in L-tryptophan productivity.

DISCLOSURE OF INVENTION

Technical Problem

The present inventors have made extensive efforts to develop a method for producing L-tryptophan with high efficiency. They have inactivated the activity of the protein represented by the amino acid sequence of SEQ ID NO: 1, which is encoded by yigL gene whose function is as yet unclear, in order to increase tryptophan producibility by inhibiting the decomposition of PLP, which is the coenzyme, and properly maintaining the intracellular PLP concentration. As a result, they have confirmed that L-tryptophan producibility was improved, thus completing the invention.

Technical Solution

An object of the present invention is to provide a microorganism of the genus *Escherichia* producing L-tryptophan. Another object of the present invention is to provide a method for producing L-tryptophan using the microorganisms producing L-tryptophan.

Advantageous Effects

The present invention provides a modified microorganism of the genus *Escherichia* producing L-tryptophan, wherein an activity of phosphatase represented by the amino acid sequence of SEQ ID NO: 1 is inactivatied. The present invention shows effects of effectively and economically producing L-tryptophan, resulting in higher yield using the microorganisms of the genus *Escherichia*. L-tryptophan produced as above may be applied not only to animal feeds or feed additives, but also to various products, such as human foods or food additives thereof, medicines, etc.

BEST MODE FOR CARRYING OUT THE INVENTION

In order to achieve the above objects, in an aspect, there is provided a modified microorganism of the genus *Escherichia* producing L-tryptophan, wherein an activity of phosphatase represented by the amino acid sequence of SEQ ID NO: 1 is inactivated. For example, the modified microorganism of the genus *Escherichia* producing L-tryptophan may be a microorganism that has increased tryptophan producibility compared to non-modified microorganisms of the genus *Escherichia*.

As used herein, the term "L-tryptophan", which refers to an α-amino acid, is an essential amino acid that is not synthesized in vivo, and is an aromatic L-amino acid whose chemical formula is $C_{11}H_{12}N_2O_2$. To increase L-tryptophan producibility in microorganisms, methods including enhancing the expression of biosynthetic enzymes in tryptophan-producing pathways and blocking side chain pathways have been used previously.

As used herein, the term "phosphatase" may refer to a protein that catalyzes reactions for removing phosphate groups from the substrates. In the present invention, "phosphatase including the amino acids of SEQ ID NO: 1", which is a protein encoded by yigL gene, is predicted to catalyze reactions that decompose PLP, which is a substrate, into pyridoxal and phosphoric acid. Since the protein encoded by yigL is named as pyridoxal phosphate phosphatase (NCBI gene ID: 12930615) on the NCBI database (http://www.ncbi.nlm.nih.gov) but phosphosugar phosphatase on the EcoCyc database (http://www.ecocyc.org), it is not known which function is a main function of the protein. According to recent research, it was reported that yigL expression is induced by heat shock (J. Gen. Appl. Microbiol., (2005) V51, pp. 93-103) and there are research results disclosing that the translation of yigL is activated by sgrS, which is a type of sRNA, thereby decomposing intracellular phosphosugars (J. Bacteriol. (2013) V195, pp. 4804-4815). However, clear functions still remain to be elucidated.

As such, the enzymes are amino acids which have a homology of 70% or higher, specifically 80% or higher, more specifically 90% or higher, even more specifically 95% or higher, even still more specifically 98% or higher, and yet even still more specifically 99% or higher with the above sequences, besides the amino acid sequence represented by SEQ ID NO: 1, and the enzymes may be included without limitation as long as they have an effect substantially the same as or corresponding to that of the above enzymes. In addition, in the case of amino acid sequences having the above homology and showing the effect corresponding to the enzyme, it is obvious that any modified enzyme having an amino acid sequence with a partial deletion, modification, substitution, or addition is included in the scope of the present invention.

The genes encoding the phosphatase represented by SEQ ID NO: 1 may be included without limitation as long as they are the sequences that can encode the enzymes and they may be indicated as yigL gene. Specifically, the genes encoding the enzymes are the nucleotide sequences having a homology of 80% or higher, specifically 90% or higher, more specifically 95% or higher, even more specifically 98% or higher, and yet even still more particularly 99% or higher with the above-listed sequences besides the nucleotide sequences represented by SEQ ID NO: 2. The gene sequences may be included without limitation as long as they encode enzymes that have an effect substantially the same as or corresponding to that of the above enzymes. In addition, in the case of the nucleotide sequences having the above homology, it is obvious that the nucleotide sequences with a partial deletion, modification, substitution, or addition are included in the scope of the present invention.

As used herein, the term "homology" refers to a percentage of identity between two polynucleotide or polypeptide moieties. The homology between sequences from a moiety to another moiety may be determined by a known technique in the art. For example, homology may be determined by directly arranging the sequence information (i.e., parameters, such as score, identity, similarity, etc.) between two polynucleotide molecules or two polypeptide molecules using a computer program (Example: BLAST 2.0) that is easily accessible and capable of arranging sequence information. In addition to this, homology between polynucleotides may be determined by hybridizing polynucleotides under the condition for forming a stable double-strand between the homologous regions and disassembling with a single strand-specific nuclease, followed by size determination of the disassembled fragments.

As used herein, the term "endogenous activity" refers to an active state of an enzyme in a natural state or before modification possessed by a microorganism.

The term "inactivate" refers to the case where the gene that encodes an enzyme is not expressed at all, compared to a strain in a natural state or before modification, and/or the case where the enzyme has the decreased or no activity even if the gene is expressed.

Thus, the inactivated activity with respect to endogenous activity refers to decreased or no activity, compared to the activity of an enzyme in a natural state or before modification originally possessed by a microorganism. The decrease is a comprehensive concept including the case where the activity of the enzyme itself is lower than the activity of the enzyme originally possessed by a microorganism due to the modification of the gene encoding the enzymes, etc.; the case where the overall level of intracellular enzymatic activity is lower than that of the strain in a natural state or before modification due to the inhibition of expression of the gene encoding the enzyme or the inhibition of translation; and a combination thereof.

The modification method for inactivating the enzymatic activity may be achieved by the application of various methods that are well-known in the art. Although not limited thereto, examples of the methods may include a method for replacing the gene encoding the enzyme on the chromosome with the gene mutated to decrease its enzyme activity, including the case where the enzyme activity is removed; a method for deleting the partial or entire gene encoding the enzyme; a method for replacing the expression control sequence for the gene encoding the enzyme with the sequence that has weak or no activity; a method for introducing a modification in the expression control sequence for the gene that encodes the enzyme on the chromosome; a method for deleting the partial or entire gene that encodes the enzyme on the chromosome; a method for introducing an antisense oligonucleotide (for example, antisense RNA), which inhibits the translation from mRNA to the enzyme by complementary binding to the transcript of the gene on the chromosome; a method for artificially incorporating a complementary sequence to the SD sequence upstream of the SD sequence of the gene that encode the enzyme, forming a secondary structure, thereby inhibiting the ribosomal attachment; and a reverse transcription engineering (RTE) method for incorporating a promoter at the 3' terminus of an open reading frame (ORF) in the corresponding sequence for reverse transcription; and a combination thereof.

Specifically, the method for deleting the partial or entire gene encoding the enzyme may be carried out by replacing the polynucleotide encoding the endogenous target protein in the chromosome with a polynucleotide or marker gene having partial deletion of nucleic acid sequences by the vectors for chromosomal insertion within bacteria. The method for deleting the genes by homologous recombination may be used as the method for deleting partial or entire genes.

As indicated above, the term "partial" may vary depending on the types of polynucleotides, but may specifically be 1 to 300, more specifically 1 to 100, and even more specifically 1 to 50, but is not limited thereto.

As indicated above, the term "homologous recombination" refers to a genetic recombination that occurs through crossover at loci of the genetic chains that have homology with each other.

Specifically, the method for modifying the expression control sequences may be carried out by inducing the modifications in the nucleic acid sequences of the expression control sequences via deletion, insertion, non-conservative or conservative substitution, or the combination thereof, or replacing with significantly weaker promoters, etc. The expression control sequences may include promoters, operator sequences, the sequences encoding ribosome-binding regions, and the sequences that control the termination of transcription and translation.

Additionally, the method for modifying the gene sequence on the chromosome may be carried out by inducing a modification in the sequence via deletion, insertion, non-conservative or conservative substitution, or a combination thereof to further decrease the enzyme activity, or replacing with the gene sequence that has been improved to have a weaker activity or gene sequence that has been improved to have no activity.

In an exemplary embodiment of the present invention, it was confirmed that various *Escherichia coli* producing tryptophan in which yigL that encodes the corresponding phosphatase has been deleted to inactivate the endogenous activity of phosphatase represented by the amino acid sequence of SEQ ID NO: 1, has increased L-tryptophan producibility compared to the parent strains where yigL has not been deleted, thereby confirming that the microorganisms of the genus *Escherichia* producing L-tryptophan, wherein the microorganism has been modified to inactivate endogenous phosphatase activity, can produce L-tryptophan effectively.

In the present invention, the microorganism of the genus *Escherichia* producing L-tryptophan refers to a microorganism that can produce L-tryptophan from carbon sources in media. Further, the L-tryptophan-producing microorganism may be a recombinant microorganism. Specifically, the types are not particularly limited as long as L-tryptophan can be produced, but the microorganism may belong to the genus *Enterbacter*, the genus *Escherichia*, the genus *Erwinia*, the genus *Serratia*, the genus *Providencia*, the genus *Corynebacterium*, and the genus *Brevibacterium*, and specifically the genus *Escherichia*.

More specifically, the microorganism of the genus *Escherichia* may be *Escherichia coli*, but the microorganism of the genus *Escherichia* that can have increased L-tryptophan producibility due to the inactivation of phosphatase activity may be included without limitation.

Specifically, in the present invention, the parent strain of the microorganism of the genus *Escherichia*, which has L-tryptophan producibility due to the inactivation of the phosphatase activity, is not particularly limited as long as it is a microorganism producing tryptophan. For example, the microorganism producing tryptophan may be modified to weaken or inactivate an activity of the gene in competitive pathways, that of regulators in tryptophan operon directional pathways, that of importer of tryptophan, and that of tryptophan influx and decomposition gene and/or to overexpress the tryptophan operon activity. The method for weakening or inactivating the activation is the same as described above, and known methods may be included without limitation. Further, known methods for the overexpression of tryptophan operon activity are included without limitation, but the examples may include a method for further inserting partial or entire gene sequences of operon genes or polynucleotides containing the expression control regions introduced from outside into chromosomes, a method for increasing copy numbers by introduction into the vector system; substitution of expression control regions that control gene expression with other control sequences; modifications where a modification in partial or entire gene sequences in the expression control regions is induced; and enhancing the operon activity by introducing modifications of the gene itself, but the examples are not limited thereto. Specifically, it may be *Escherichia coli* in which partial or entire pheA, trpR, mtr, and/or tnaAB genes have been deleted and/or tryptophan operon has been overexpressed.

In the present invention, besides pheA, trpR, mtr, and tnaAB genes, tryptophan operons, and protein sequences encoded by these, the gene sequences and protein sequences used for the present invention may be recovered from known databases (i.e., GenBank of NCBI, etc.), but the examples are not limited thereto. In addition, detailed information about pheA, trpR, mtr, and tnaAB genes, etc., can be referred to from the contents disclosed in Korean Patent No. 10-0792095 and Korean Patent Publication No. 10-2013-0082121, and the entire specification may be included as a reference for the present invention.

With respect to the exemplary embodiment of the present invention, as a result of inactivating the phosphatase activity in various parent strains, in the case of the microorganism of the genus *Escherichia* producing L-tryptophan, it was confirmed that L-tryptophan producibility was significantly improved when the phosphatase activity was inactivated regardless of the types of parent strains.

In another aspect of the present invention, there is provided a method for producing L-tryptophan including culturing the modified microorganism of the genus *Escherichia* producing L-tryptophan in a medium, wherein an activity of phosphatase represented by the amino acid sequence of SEQ ID NO: 1 is inactivated; and recovering L-tryptophan from the cultured microorganism and the medium.

Any media or culture conditions used for culturing the microorganism of the present invention may be used without limitation as long as they are conventional media used for culturing the microorganism of the genus *Escherichia*, but specifically, the microorganism of the present invention can be cultured in conventional media containing adequate carbon sources, nitrogen sources, phosphorus sources, inorganic compounds, amino acids and/or vitamins, etc., under aerobic conditions while controlling temperature, pH, etc.

In the present invention, the carbon sources may include carbohydrates, such as glucose, fructose, sucrose, maltose, mannitol, sorbitol, etc.; alcohols such as sugar alcohols, glycerol, pyruvic acid, lactic acid, citric acid, etc.; and amino acids such as organic acids, glutamic acid, methionine, lysine, etc. Further, natural organic nutritional sources, such as corn starch hydrolysates, molasses, blackstrap molasses, rice bran, cassava, sugar cane residues, and corn steep liquor, may be used, and specifically, carbohydrates, such as glucose, sterile pre-processed molasses (that is, molasses transformed to reducing sugars, etc.) may be used, and an adequate amount of carbon sources besides the list may be widely used without limitation. These carbon sources may be used alone or in combination of at least two types, but are not limited thereto.

For the nitrogen sources, inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources such as peptone, NZ-amine, meat extracts, yeast extracts, malt extracts, corn steep liquor, casein hydrolysates, fish or the decomposition product thereof, and defatted soybean cake or the decomposition product thereof may be used. These nitrogen sources may be used alone or in combination of at least two types, but are not limited thereto.

For the phosphorus sources, monopotassium phosphate, dipotassium phosphate, the corresponding sodium-containing salts, etc. may be included. For inorganic compounds, sodium chloride, calcium chloride, iron chloride, magnesium sulfate, iron sulfate, manganese sulfate, calcium carbonate, etc. may be used, and besides, amino acids, vitamins, proper precursors, etc. may be included. These media or precursors may be added to the culture products as a batch culture or continuous culture.

In the present invention, during culturing of microorganisms, compounds such as ammonium hydroxide, potassium hydroxide, ammonia, phosphoric acid, sulfuric acid, etc. may be added to the culture products by appropriate methods in order to regulate pH of the culture products. Further, in the process of culturing, antifoaming agents such as fatty acid polyglycol ether may be used to inhibit foam formation. In addition, oxygen or an oxygen-containing gas may be injected into the culture product to maintain aerobic conditions of the culture products, or nitrogen, hydrogen, and carbon dioxide gases or no gases may be injected to maintain anaerobic and microaerophilic conditions.

The temperature of the culture products may specifically range from 27° C. to 40° C., more specifically from 30° C. to 37° C., but is not limited thereto. The culturing may be continued until the desired production output of the useful products is recovered, and may be continued specifically for 10 hours to 100 hours, but is not limited thereto.

The above step for recovering L-tryptophan may recover the desired L-tryptophan from the cultured microorganism and the culture medium using the culture methods of the present invention, for example, batch culture, continuous culture, fed-batch culture, etc., based on the appropriate methods known in the technical field. The recovery step may include a purification process. The purification process may purify the recovered L-tryptophan using the appropriate methods known in the art.

Mode for Carrying out the Invention

Hereinafter, the present invention will be described in detail with reference to the following Examples. However, these Examples are for illustrative purposes only, and the scope of the present invention is not limited to these Examples.

EXAMPLE 1

Preparation of Phosphatase-deficient Wild-type Strain

In this example, a strain where phosphatase activity was inactivated was prepared from a strain producing tryptophan.

yigL gene, which was predicted to encode phosphatase, was deleted by homologous recombination in W3110 trpΔ2 strain (Korean Patent Application Publication No. 10-2013-0082121), where pheA gene (NCBI gene ID: 12934467) encoding chorismate mutase/prephenate dehydratase (CM-PDT), tnaA gene (NCBI gene ID: 12933600) encoding tryptophanase, and tnaAB gene, which are operon forms of the tnaB gene (NCBI gene ID: 12933602) that encodes tryptophan importer, were deleted from W3110 strain, which is an *Escherichia coli* wild-type strain, a representative microorganism of the genus *Escherichia*, in order to enhance tryptophan producibility.

Specifically, a one-step inactivation method involving lambda red recombinase developed by Datsenko KA, etc. was used to delete yigL gene containing the gene sequences of SEQ ID NO: 2 (Proc Natl Acad Sci USA, (2000) V97, pp 6640-6645). As for the markers for confirming the insertion into the genes, the rmf promoters were ligated to pUC19 (New England Biolabs (USA)), and chloramphenicol genes of pUCprmfmloxP, which was recovered by the ligation of mutated loxP-CmR-loxP cassette recovered by pACYC184 (New England Biolab), were used (Korean Patent Publication No. 10-2009-0075549).

Firstly, the pUCprmfmloxP was designated as a template using the combination of primers of SEQ ID NOS: 3 and 4 containing partial yigL gene and partial gene sequences of chloramphenicol resistance gene of the pUCprmfmloxP gene. Then, AyigLlst, a polymerase chain reaction (hereinafter 'PCR') product of about 1.2 kb was recovered by the primary PCR, which repeated 30 cycles of denaturation at 94° C. for 30 seconds, annealing at 55° C. for 30 seconds, and polymerization at 72° C. for 1 minute. Later, the AyigLlst, the PCR product of about 1.2 kb recovered from the PCR, was subjected to electrophoresis on 0.8% agarose gel, eluted, and used as a template for the secondary PCR. During the secondary PCR, ΔyigL, a PCR product of about 1.3 kb, was recovered by repeating 30 cycles of denaturation at 94° C. for 30 seconds, annealing at 55° C. for 30 seconds, and polymerization at 72° C. for 1 minute using the combination of primers of SEQ ID NOS: 5 and 6 containing 20 bp of the gene sequences in the 5' and 3' regions of the PCR products that were recovered from the primary PCR, while using the eluted primary PCR products as a template. The thus-recovered PCR product was subjected to electrophoresis on 0.8% agarose gel, eluted, and used for recombination.

*Escherichia coli* W3110 trpΔ2 transformed to pKD46 vector was prepared in a competent state according to the one-step inactivation method (Proc Natl Acad Sci USA., (2000) V97, pp. 6640-6645) developed by Datsenko KA, etc. and was then transfected by the 1.3 kb-long ΔyigL fragments recovered from the primary and secondary PCR. Later, they were cultured in LB media containing chloramphenicol, and primary transfectants having chloramphenicol resistance were selected.

After removing pKD46 from the thus-recovered primary recombinant strains having chloramphenicol resistance, chloramphenicol marker genes were removed from bacteria (Gene, (2000) V247, pp. 255-264) by introducing pJW168 vectors (Gene, (2000) V247, pp 255-264). It was confirmed that the yigL gene was deleted by PCR products of about 0.6 kb recovered from the finally-recovered bacteria through the PCR, using the primers of SEQ ID NOS: 7 and 8, and named as W3110 trpΔ2 yigL.

The primer sequences used in this Example are shown in Table 1 below.

TABLE 1

| Primer | Sequence | SEQ ID NO |
|---|---|---|
| yigL-Cm-R2 | ttgcgtctgatttagatggcacgttactttctccc gaccatacgttatcctagtggatctgatgggtacc | 3 |
| yigL-R1 | cccagcggaaaccgctctacagaggtttaaatttc ttatgtaccaggttgttgcgtctgatttagatggc | 4 |
| yigL-Cm-F2 | ccattgtagcgaagtatcaggttgacaactgacca aataaagaacgattaaggtgacactatagaacgcg | 5 |
| yigL-F1 | tggtgatgataagtagcgccacaatggaaaactat tgattaacgggtatccattgtagcgaagtatcag | 6 |

TABLE 1-continued

| Primer | Sequence | SEQ ID NO |
|---|---|---|
| yigL conF1 | aaccgcatgcatgaccgttt | 7 |
| yigL conR1 | atatacaggccgaccgtttt | 8 |

EXAMPLE 2

Production of Tryptophan-producing Strains with Inactivated Phosphatase

In this example, yigL gene, which was predicted to encode phosphatase, was deleted by homologous recombination as described in the method of Example 1, while having KCCM11166P (Korean Patent No. 10-1261147), which is another representative *Escherichia coli* that produces tryptophan, as a parent strain.

It was confirmed that the yigL gene was deleted by PCR products of about 0.6 kb recovered from the finally-recovered bacteria through the PCR using the primers of SEQ ID NOS: 7 and 8, and named as CA04-2803.

EXAMPLE 3

Evaluation of Tryptophan Productivity of yigL Gene-deficient Wild-type Strains pCL-Dtrp_att-trpEDCBA and pBAC-Dtrp_att-trpDCBA were introduced into each strain by transformation methods to compare tryptophan productivity between W3110 trpΔ2 yigL produced in Example 1 and W3110 trpΔ2, which is a parent strain. The introduced vectors were the vectors having enhanced expression of tryptophan operons for tryptophan overproduction by releasing the control mechanism in tryptophan operon control regions (Korean Patent Publication No. 10-2013-0082121). The strains with introduced vectors were cultured on the tryptophan test medium that was prepared according to the composition of Table 2 and their L-tryptophan-producing activities were compared.

TABLE 2

| Composition of tryptophan test medium | |
|---|---|
| Composition | Conc. (per liter) |
| Glucose | 2 g |
| K₂HPO₄ | 1 g |
| (NH₄)₂SO₄ | 12 g |
| NaCl | 1 g |
| Na₂HPO₄•H₂O | 5 g |
| MgSO₄•H₂O | 1 g |
| MnSO₄•H₂O | 15 mg |
| CuSO₄•H₂O | 3 mg |
| ZnSO₄•H₂O | 30 mg |
| Sodium citrate | 1 g |
| Yeast extract | 1 g |
| Phenylalanine | 0.15 g |
| pH | 6.8 |

The strains, which were cultured overnight on LB solid medium in a 37° C. incubator, were inoculated into the 25 mL test medium of Table 2 by one platinum loop, respectively, and cultured for 48 hours in a 37° C. incubator at 200 rpm. Then, tryptophan concentrations were compared (Table 3).

TABLE 3

| Strain | Tryptophan Conc. (g/L) |
|---|---|
| W3110 trpΔ2/pCL-Dtrp_att-trpEDCBA, pBAC-Dtrp_att-trpDCBA | 0.5 |
| W3110 trpΔ2 yigL/pCL-Dtrp_att-trpEDCBA, pBAC-Dtrp_att-trpDCBA | 0.8 |

The results above show that the strain in which the activity of phosphatase encoded by yigL gene was inactivated showed a 60% increase in tryptophan productivity compared to the strain in which the phosphatase activation was not inactivated. It was confirmed that the tryptophan productivity could be improved by the inactivation of phosphatase, which is encoded by yigL. This could be interpreted to mean that tryptophan biosynthesis was increased due to the increase in the concentration of PLP, which plays a crucial role as a coenzyme important for tryptophan biosynthesis, because of the inactivation of phosphatase, which is encoded by yigL.

EXAMPLE 4

Evaluation of Tryptophan Productivity of yigL Gene-deficient Strains

To measure the tryptophan titer of the yigL-deficient strain (CA04-2803) produced in Example 2 and KCCM11166P, which is the parent strain, the strain was cultured in tryptophan titer medium that was prepared according to the composition of Table 4 shown below. Then, the enhanced L-tryptophan production efficiency was confirmed.

TABLE 4

| Composition of tryptophan titer medium | |
|---|---|
| Composition | Conc. (per liter) |
| Glucose | 60 g |
| K₂HPO₄ | 1 g |
| (NH₄)₂SO₄ | 10 g |
| NaCl | 1 g |
| MgSO₄•7H₂O | 1 g |
| Sodium citrate | 5 g |
| Yeast extract | 2 g |
| Calcium carbonate | 40 g |
| Sodium citrate | 5 g |
| Phenylalanine | 0.15 g |
| Tyrosine | 0.1 g |
| pH | 6.8 |

The *Escherichia coli* strains, KCCM 11166P and CA04-2803, which were cultured overnight in LB solid medium in a 37° C. incubator, were inoculated into the 25 mL titer media of Table 4 by one platinum loop, respectively, and cultured for 48 hours in a 37° C. incubator at 200 rpm. Then, the glucose consumption rate and tryptophan concentrations were compared.

As a result, as indicated in Table 5 shown below, the tryptophan concentration of CA04-2803, which is a strain with inactivated phosphatase encoded by yigL gene, showed an increase in tryptophan concentration of about 30%, compared to the control, KCCM11166P.

TABLE 5

| Strain | Tryptophan Conc. (g/L) |
|---|---|
| KCCM11166P | 7.48 |
| CA04-2803 | 9.62 |

The present inventors have confirmed that tryptophan productivity has been increased in the inactivated strains that are deficient in yigL that encodes phosphatase and are KCCM11166P strain-based. The strains were named as "CA04-2803" or "CA04-2803 (KCCM11166P_ΔyigL)" and deposited with the Korean Culture Center of Microorganisms, recognized as an international depository authority under the Budapest Treaty on Dec. 5, 2014, under the accession number, KCCM11635P.

The above results suggest that L-tryptophan productivity was increased more in the strain with inactivated phosphatase activity, compared to the strain without the inactivation of phosphatase, in the microorganism of the genus Escherichia producing L-tryptophan. Further, such results regarding the increase in tryptophan production are caused by the inactivation of phosphatase that is encoded by yigL and are considered to be caused by the inactivated function of PLP phosphatase, which is one of the anticipated functions of phosphatase encoded by the gene. This is highly likely due to the increased intracellular PLP concentration.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A modified microorganism of the genus *Escherichia* producing L-tryptophan, wherein the activity of phosphatase comprising the amino acid sequence of SEQ ID NO: 1 is inactivated.

2. The microorganism according to claim 1, wherein the microorganism of the genus *Escherichia* is *Escherichia coli*.

3. A method for producing L-tryptophan, comprising:
   (i) capturing the microorganism of the genus *Escherichia* of claim 1 in a medium; and
   (ii) recovering L-tryptophan from the cultured microorganism and the medium.

4. A method for producing L-tryptophan, comprising:
   (i) capturing the microorganism of the genus *Escherichia* of claim 2 in a medium; and
   (ii) recovering L-tryptophan from the cultured microorganism and the medium.

* * * * *